US006485747B1

(12) United States Patent
Flanagan et al.

(10) Patent No.: US 6,485,747 B1
(45) Date of Patent: Nov. 26, 2002

(54) COATED ACTIVE TABLET(S)

(75) Inventors: John Flanagan, Neshanic Station, NJ (US); Terry L. Smith, Pottstown, PA (US); Aaron Barkley, Willow Grove, PA (US); Richard E. Nicholson, Birdsboro, PA (US); Timothy Patrick Callahan, Malvern, PA (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/416,181

(22) Filed: Oct. 11, 1999

Related U.S. Application Data

(63) Continuation-in-part of application No. PCT/US98/23430, filed on Oct. 30, 1998, and a continuation-in-part of application No. 09/308,043, filed on Sep. 24, 1999, now Pat. No. 6,395,298.

(51) Int. Cl.$^7$ ............................ A61K 9/34; A61K 47/36
(52) U.S. Cl. ..................... 424/479; 424/481; 514/777
(58) Field of Search ............... 424/479, 481, 424/493, 496; 427/2.14, 2.17, 2.18, 2.2; 514/777

(56) References Cited

U.S. PATENT DOCUMENTS

| 4,326,052 A | | 4/1982 | Kang et al. |
| 4,385,123 A | | 5/1983 | Kang et al. |
| 5,334,640 A | | 8/1994 | Desai et al. |
| 5,474,759 A | * | 12/1995 | Fassberg et al. |
| 5,681,577 A | * | 10/1997 | Lech et al. |
| 5,879,712 A | * | 3/1999 | Bomberger et al. |

FOREIGN PATENT DOCUMENTS

| EP | 0048123 | 3/1982 |
| EP | 0 630 580 | 12/1994 |
| JP | 62-125850 | 6/1987 |
| JP | 62132831 | 6/1987 |
| JP | 62-132831 | 6/1987 |
| JP | 09-020649 | 1/1997 |
| WO | WO 94/18954 | 9/1994 |
| WO | 9922769 | 5/1999 |

OTHER PUBLICATIONS

"Gellan Gum Coating and Adhesion Systems" Research Disclosure, Kelco Division of Merck and Co., Inc. Jun. 1993.

PCT/US00/28032/International Search Report, dated Feb. 2001.

Research Disclosure, GB, Industrial Opportunities Ltd., "Simple Films and Coatings Made With Gellan Gum", No. 361, p. 224, 225, XP000453954, dated May 1994.

Monsanto: "Kelcogel Gellan Gum" www.NutrasweetKelco.com, Online, 1998 XP002159570, retrieved from the Internet Feb. 2001.

* cited by examiner

*Primary Examiner*—Edward J. Webman
(74) *Attorney, Agent, or Firm*—Banner & Witcoff Ltd.

(57) ABSTRACT

A tablet coating useful for coating an active selected from the group consisting of aspirin, ibuprofen, naproxin sodium, acetaminophen, celecoxib, sildenafil citrate, alendronate sodium, an analgesic in combination with one or more of an antitussive, antihistamine, decongestant and expectorant, oxaprozin, comprising gellan gum along with a process which comprises admixing gellan gum and water under effective shear conditions to prepare an aqueous gellan gum coating composition thereof whereby the aqueous gellan gum coating composition is applied in an adherent fashion to a placebo or a tablet containing an active to form a gellan gum coated placebo or gellan gum coated active.

18 Claims, No Drawings

COATED ACTIVE TABLET(S)

This application is a continuation in part of PCT/US98/23430 filed Oct. 30, 1998 and of U.S. patent application Ser. No. 09/308,043 filed Sep. 24, 1999, now U.S. Pat. No. 6,395,298 both of which are incorporated herein in their entirety by reference.

FIELD OF THE INVENTION

This invention relates generally to tablet coating(s) on active drugs and to a method to prepare compositions useful to coat active drugs. More particularly this invention relates to a drug coated with gellan gum, a method to prepare a gellan gum composition useful to coat an active drug, a gellan gum composition useful to coat an active drug(s), and to a method for coating active drugs(s) with gellan gum. In particular this invention relates to an intact active tablet comprising an active ingredient selected from the group consisting of aspirin, naproxen sodium, acetaminophen, ibuprofen, celecoxib, oxaprozin, sildenafil citrate, alendronate sodium, mixtures thereof and the like and optimally an analgesic in combination with one or more of an antihistamine, antitussive, decongestant, and expectorant and mixtures thereof and the like, coated with gellan gum, a method to prepare a gellan gum composition useful to coat one or more of the aforementioned actives, mixtures thereof and the like, and to a method for coating one or more of the aforementioned actives, mixtures thereof and the like, with gellan gum.

BACKGROUND OF THE INVENTION

Tablets are typically used to deliver a pharmacologically effective amount of a therapeutic active (drug) to humans and animals so as to provide medicinal benefit to the human or animal. Typically such therapeutically effective drugs include those drugs that possess and produce desirable drug effects after effective consumption by the human or animal. Effective consumption is achieved by oral or rectal administration to a patient for example.

In medicinal uses, one or more coatings is desired on a medicinal tablet in order to obtain one or more of gloss, better appearance, identification, mouthfeel, stability, color, swallowability, improved taste and the like.

Many medicinal tablet coatings today are low viscosity hydroxypropylmethylcellulose (HPMC). Usually a HPMC solution of about 10% weight with a viscosity below 1000 cps. (centipoise), with appropriate plasticizer, is applied by a spraying system or device to a tablet in a coating process.

Even with the foregoing and other tablet coating compositions, the industry continues to desire a product(s) which provides enhanced tablet coating properties on an active but a coating that can be applied with conventional equipment in a comparable or shorter period of time than existing technologies and systems, providing an intact coated tablet which has been effectively coated with gellan gum at a relatively low coating amount and achieving a low weight gain. The industry has recognized the need for an improved intact tablet coating especially for the aforementioned activities, which would provide increased gloss, better mouthfeel at coating quantities at lower levels than conventionally accepted methods, for example. The process of preparing such an improved tablet coating for the aforementioned activities economically and efficiently continues to be of interest.

OBJECTS OF THE INVENTION

It is an object of this invention to provide an intact active tablet with an active ingredient(s) wherein said active is selected from the group consisting of aspirin, naproxin sodium, naproxin sodium, acetaminophen, celecoxib, oxaprozin, sildenafil citrate, alendronate sodium, analgesic in combination with another drug, and the like, coating comprising gellan gum and gellan gum combinations.

It is another object of this invention to provide one or more ingredients (from the aforementioned active ingredients) coated with gellan gum.

It is an additional object of this invention to provide a process for preparing a gellan gum composition useful for coating such one or more of the aforementioned actives.

It is yet an additional other object of this invention to provide a process for preparing one or more such actives having a coating comprising gellan gum.

It is still another object of this invention to provide an improved process for preparing a gellan gum composition useful for coating such active drugs.

It is yet still an additional object of this invention to provide an active tablet having one or more enhanced properties such as being intact, having higher gloss, having better mouthfeel, possessing non-tackiness, being swallowable with little or no accompanying liquid having better taste and the like.

The above objects and other objects are met in this invention which is more particularly described hereinafter without limitation.

BRIEF SUMMARY OF THE INVENTION

In one embodiment, this invention comprises an intact active tablet with an active ingredient selected from the group consisting of aspirin, naproxen sodium, acetaminophen, ibuprofen, celecoxib, oxaprozin, sildenafil citrate, alendronate sodium, an analgesic in combination with one or more of an antitussive, antihistamine, decongestant and expectorant, mixtures thereof and the like having a coating comprising gellan gum. In another embodiment this invention further comprises a process for preparing a gellan gum composition useful for coating such an active such as those mentioned herein which comprises the steps of drixing gellan gum and water under effective shear conditions to prepare an aqueous gellan gum coating composition thereof. In another embodiment this invention further comprises preparing the aforementioned aqueous gellan gum coating composition and applying the same in an adherent fashion such as to one or more of the actives mentioned herein whereby a gellan gum coated intact active tablet is formed and thereafter optionally drying the same. In yet another embodiment of this invention, this invention comprises a method of treatment for a patient (in need of treatment) which comprises administering to a patient a therapeutically effective amount of a coated intact tablet active such as those mentioned herein, wherein said coated intact active tablet comprises an active such as these mentioned herein coated with gellan gum and which contains a therapeutically effective amount of active(s) beneficial to said patient.

Other embodiments of this invention are included herein and are described in more detail hereinafter.

DETAILED DESCRIPTION OF THE INVENTION

Gellan gum useful herein is that produced by inoculating a carefully formulated fermentation medium with the microorganism Sphingamonas-elodea (ATTC 31461). Gellan Gum is available from Monsanto Company, 800 North Lindbergh Boulevard, St. Louis, Mo. 63167, USA. Typical brand names include KELCOGEL® and GELRITE®. However, Gellan gum useful herein includes any available form such as but not limited to, non-clarified, clarified, and partially-clarified native, deacetylated and partially deacetylated forms as well as mixtures thereof and the like which are made up of constituent sugars (Glucose, Glucuronic acid and Rhamnose) in a molar ratio of 2:1:1 and are linked together to give a primary structure consisting of a linear tetrasaccharide repeating unit. Kelcogel® and Gelrite® are registered trademarks of Monsanto Company, 800 North Lindbergh Blvd., St. Louis, Mo., 63167 U.S. Gellan gum may be prepared according to the methods disclosed in U.S. Pat. Nos. 4,326,052 and 4,385,123 both of which are incorporated herein their entirety by reference.

Optional components of the gellan gum aqueous coating composition of this invention may include but are not limited to a color additive(s) and/or other coating polymers as will be readily apparent to those of skill in the art in particular after reading this specification. A typical plasticizer is propylene glycol or polyethylene glycol although any equivalent or substantially equivalent plasticizer may be satisfactorily employed herein if desired.

The scope and utility of the present invention is not limited to any active ingredient. Active ingredients which may be effectively coated using this invention are not limited and include illustratively pharmaceutical active ingredients and over-the-counter drugs (including vitamins and nutritional supplements and the like) such as those typically delivered in a tablet dosage form. Examples include but are not limited to analgesics, anti-inflammatory's and antipyretics such as aspirin, acetaminophen, ibuprofen, naproxyn sodium, phenacetin; celecoxib, oxaprozin, sildenafil citrate, alendronate sodium, steroids including anti-inflammatory steroids; and combination product(s) where one or more analgesics are combined with one or more of antihistamines, decongestants, antitussives and/or expectorants, mixtures thereof and the like.

Examples of the latter include and are not limited to:

Decongestants (Pseudoephedrine, Phenylpropanolamine, Ephedrine, Epinephrine, Phenylephrine, Naphazoline, Xylometazoline, Oxymetazoline); Antitussives (Codeine, Dextromethorphan, Diphenhydramine, Benzonatate, Chlophedianol, Noscapine, Carbetapentane Citrate); Expectorants (Guaifenesin, Iodine Products, Terpinhydrate, Ammonium Chloride, Beechwood Creosote, Potassium, Guaiacolsufonate, Syrup Ipecac); and Atnihistamines (Pheniramine, Thonzylamine, Phenyltoloxamine, Doxylamine, Diphenhydramine, Carbinoxamine, Clemastine, Tripelennamine, Pyrilamine Maleate, Chlorpheniramine, Dexchlorpheniramine, Brompheniramine, Triprolidine, Promethazine, Trimeprazine, Methdilazine, Cylcoheptadine, Azatadine, Diphenylpyraline, Phenindamine).

For brevity of text only, hereinafter, particularly with respect to the process description hereinafter, the term "aspirin" is employed hereafter in the specification. However these of skill in the art will immediately recognize that the term "aspirin" hereafter includes without limit ibuprofen, naproxen sodium, acetaminophen, sildenafil citrate, celecoxib, oxaprozin, alendronate sodium, mixtures thereof and the like as well as an analgesic in combination with an antihistamine, antitussive, decongestant and expectorant, mixtures thereof and the like. The process description hereafter following pages 6–17 following with respect to aspirin or a tablet applies likewise to one or more of to ibuprofen, naproxen sodium, acetaminophen, sildenafil citrate, celecoxib, alendronate sodium, mixtures thereof and the like without limit and to other medicines such as an analgesic in combination with an antihistamine, antitussive, decongestant, expectorant, mixtures thereof and the like. However, in these Examples the word aspirin there means aspirin itself.

The process for preparing a coated aspirin (or another active as aforementioned) of this invention comprises the steps of admixing gellan gum and water under effective shear, heat and ionic conditions to prepare an aqueous gellan gum coating composition and applying the aqueous gellan gum coating composition in an effective fashion to a receptive placebo or to a tablet such as one comprising a pharmaceutical whereby a gellan coated tablet is formed. A drying step typically occurs and typically follows.

The aqueous gellan gum coating composition useful to coat aspirin (and other actives mentioned herein) is preferably admixed in any suitable container or the like prior to applying the gellan gum composition to or on an aspirin tablet to be coated. Initially the gellan gum and water are admixed and further mixing is carried out under effective shear to form an aqueous aspirin tablet coating composition. The aspirin tablet to be coated employing this invention is receptive to the gellan gum coating composition of this invention. Typically the gellan gum coating aqueous composition prior to application of such effective shear will have a viscosity in the range from about 44 cps. to about 55,500 cps. and preferably from about 2200 to about 50,000 cps. although gellan gum compositions having greater and lesser viscosities may sometimes be employed depending on a number of factors including but not limited to temperature.

If desired, gellan gum compositions comprising gellan gum and/or gellan gum and one or more of another ingredient such as a polymer such as, but not limited to, those selected from the group consisting of hydrocolloids and galactomannans and acrylics, hydroxypropyl methyl cellulose, hydroxypropyl cellulose, sodium carboxymethyl cellulose, sugar, aspartame, maltodextrin, tapioca dextrin, modified food starches, polyvinylpyrolidone, mixtures thereof and the like may be employed in this invention. As employed herein, the term "gellan gum" includes gellan gum and/or compositions of gellan gum with one or more of these polymers, starches, acrylics, or a sugar.

The aqueous gellan gum composition of this invention may be mixed in or by any suitable mixing system preferably until substantially complete mixing has been accomplished. Some heating may be necessary to achieve dispersion and hydration of gellan gum. The amount of shear preferably employed is an effective amount, i.e., which produces a well mixed homogenous gellan gum composition. The aforementioned admixing can be carried out by any convenient means including but not limited to use of a propeller or stirrer system although generally stirring by a convenient mechanical means is acceptable. Other forms of mixing can be employed.

If desired, one or more applications of the coating composition may be made to an aspirin tablet to be coated or to a coated aspirin tablet. The amount of gellan gum in such composition may be varied from application to application or kept the same or substantially as desired.

Optionally, if desired, various other ingredients may be employed in the gellan gum aqueous composition include any ingredient which is compatible or can be made compatible with an aqueous gellan gum composition useful to coat tablets of this invention, (such as, but not limited to, colors, color system(s), flavor(s), sweetener(s), mint(s), fragrance(s), plasticizer(s), active ingredient(s) and mixtures thereof and the like).

The gellan gum aqueous composition of this invention is preferably applied to the aspirin tablet(s) (and other actives mentioned herein) to be coated in a batch, semi-continuous or continuous process or some combination thereof in a manner which produces a satisfactorily and usually uniformly coated tablet. The gellan gum composition may be applied to aspirin (and/or other active(s)) tablets to be coated using any satisfactory application and drying system or combination of some application system and some drying system. The combination is not critical nor is the arrangement of equipment.

The amount of gellan gum in the gellan gum aqueous composition useful for coating aspirin tablets and other actives is in the range from about 0.5% to about 10% and preferably from about 0.5% to about 5% by weight gellan gum of the total gellan gum aqueous composition although greater and lesser amounts of gellan gum may be employed if desired. A most preferred range is about 0.5% to about 3% by weight.

During application of the gellan gum aqueous composition to the tablet to be coated, the temperature of the gellan gum aqueous composition is preferably in the range from about 25° C. to about 50° C. although greater or lesser temperatures may be employed if desired. It is preferred that the gellan gum composition be maintained in a solution or dispersion or an applicable state during its coating application to the aspirin tablet(s) to carry out this invention.

Historically those of skill in the art have considered a composition having a viscosity of about 1,000 centipoise (cps) as being at the upper bound as regards usefulness as a coating composition due to that high viscosity and inability to spray. Since an aqueous composition comprising gellan gum (1.8% by weight gellan gum) and water has a viscosity of about 28,460 cps at a temperature of about 30° C., those of skill in the art would not have considered such a composition useful to coat tablets and would have been steered away from it for this invention. Now, however, the inventors have surprisingly discovered that despite the high viscosity of a gellan gum composition at room temperature that such compositions are very useful to coat aspirin tablets as the invention herein provides.

Gellan gum may be coated onto aspirin tablets and other actives mentioned herein which are uncoated or are those tablets which have been coated with one or more prior coatings (overcoating) of an acceptable coating composition which allows adherency with gellan gum. An initial coating may comprise one or more polymers such as cellulosics, dextrins, starches, acrylics, any colors or other pharmaceutical coating material. A gellan gum composition may be employed as a primary coating on a tablet, as a secondary coating on a tablet, or as a tertiary coating if desired. One or more coating applications of gellan gum may be made to a coated or uncoated tablet in accordance with this invention, although typically one coating is effective and is preferred. If desired, a gellan gum coating may be applied to a tablet in accordance with the invention in an instance wherein a protective coating is desired, for example to protect coated or uncoated tablet from physical damage.

Typically the amount of gellan gum which is coated onto tablets in practicing this invention is that amount which provides a gellan gum coated tablet having a weight gain (during coating) in the range or about 0.025% to about 10% weight percent of the total tablet weight and preferably from about 0.05% to about 5% weight percent of the total tablet weight and most preferably from about 0. 1% to about 1% wt. percent of the total tablet weight although larger and smaller weight percents may be employed if desired. Typically this amount of gellan gum is that amount which is necessary to provide an effective or desired coating.

Neither the tablet shape nor the tablet size are critical. Preferred shapes and sizes are those which can be effectively consumed by a human or animal recipient with relative ease. Preferable sizes of tablets include but is not limited to those tablets which are about ⅛ inch to about 1 inch in size and weigh from about milligrams to about 2 grams each although tablets may be employed which are larger or smaller in size and of lighter and heavier weight if desired. Preferred shapes are round or oval; however, other shapes may be employed if desired.

Preferred tablets are medicinal tablets for humans or animals. The tablets include but are not limited to tablets of any convenient composition which may or may not contain any pharmaceutically effective drug, vitamin or nutrient or drugs suitable for human and/or animal consumption. A gellan gum coating may be employed on tablets which are placebos or blanks. Tablets useful herein include but are not limited to tablets which are uncoated or have been coated one or more times. Useful actives include but are not limited to ibuprofen, aspirin, naproxen sodium, celecoxib, oxaprozin, sildenafil citrate, alendronate sodium, mixtures thereof and the like. In one embodiment a gellan gum coating may be the only coating and may also comprise a first coating or a second or a third coating or primary coating. In another embodiment gellan gum may be the only coating and the gellan gum coating may be the primary coating or comprising only gellan gum.

Illustrative colors and colorants useful herein include without limitation, pigments, dyes, lakes and oxides (including titanium dioxide) and the like, may be optionally employed with gellan gum used in practicing this invention. The gellan gum aqueous composition may optionally contain a suitable color or colorants for application to a colored or noncolored coated or uncoated tablet.

Tablets to be coated according to this invention may be colored, neutral or have their natural color or may be absent color. If one of more colors, dyes lakes, or pigments or mixtures thereof are employed in a gellan gum coating composition herein, such as for example, an FDA certified color, dye, lake, or pigment, the color or combination of colors is not critical and may be selected by those of skill in the art based upon a need at the time of the coating operation. Examples of suitable pigments which are useful in this invention include, without limitation, FD&C and D&C lakes, titanium dioxide, magnesium carbonate, talc, pyrogenic silica, iron oxides, channel black, insoluble dyes and mixtures thereof and the like. Also, nature pigments such as riboflavin, carmine 40, curcumin, annatto, mixtures thereof and the like are acceptable herein. Other examples of pigments suitable herein include, without limitation, these disclosed in Jeffries U.S. Pat. No. 3,149,040 and Butler et al., U.S. Pat. No. 3,297,535, as well as in Colorcon U.S. Pat. No. 3,981,984. These three patents are incorporated herein by reference in their entirety. In the absence of a colorant, the gellan gum composition typically produces a clear or substantially clear coating on a coated tablet.

As employed herein, the term "tablet" includes without limitation, tablet, caplet, particle, micronized particle, particulate, pellet, pill, core, powder, granule, granulate, small mass, seed, specks, spheres, crystals, beads, agglomerates, mixtures thereof and the like. Typically the, preferred tablet will be in a form sufficiently stable physically and chemically to be effectively coated in a system which involves some movement of the tablet, as for example in a fluidized bed, such as in a fluidized bed dryer or a side vented coating pan, combinations thereof and the like. Virtually any tablet, placebo, the latter typically lactose or sugar or mixtures thereof and the like, is acceptable herein as a tablet to be coated in the practice of this invention.

Tablets coated according to this invention have a high gloss. Typically the gloss is in the range from about 200 to about 400 and preferably from about 250 to about 350 although greater or lesser gloss may be employed if desired. As referred to above, gloss is measured or characterized typically by use of a Tricor Systems, Inc., Model 805A, Surface Analysis System. Tablets of this invention typically have one or more enhanced properties such as higher gloss, better mouthfeel, non-tackiness, being swallowable with little or no accompanying liquid, better taste and the like.

The gloss resulting from gellan gum coating of this invention is superior in shine to conventional film coatings presently used in the industry. Measurements of gloss on polymer coated tablets and commercial products were well below the gloss imparted with gellan gum prepared in accordance with this invention as measured at TRICOR Systems. Gellan gum coatings of this invention impart this gloss at weight gain levels that are considerably lower than existing and accepted alternatives. As a result of this high gloss from comparatively lower weight gains brought about by this invention, gellan gum is an attractive alternative to existing aqueous form coatings.

This characteristic high gloss from low weight gains also makes gellan gum an attractive alternative to sugar coating processing currently used in the industry. Sugar coating processes currently use multiple materials, extended processing times and multiple material handling steps. Superior gloss can be achieved with gellan gum at a fraction of the weight gain now required in sugar coating. This lower material requirements results in glossy tablets that can be manufactured much faster than current products and can also be formulated to produce a smaller, easier to swallow dosage.

As employed herein, the term "adherent" means that the gellan gum coating effectively adheres to the coated tablet until consumption by a patient or animal to enable effective release of the active ingredient therefrom so that the active ingredient(s) is/are effectively made available to the patient's biological systems within established acceptable time frames so as to provide therapeutic value and thus meet acceptable dissolution and disintegration testing time frames.

Although the gellan gum coating composition of this invention will initially be an aqueous composition, the tablet coating will preferably be dried or substantially dried prior to, upon its exit or removal from the coating application system or at sometime in preparing coated tablets. The coated tablets may be placed in suitable packaging then if desired.

The amount of coating provided to the surface of the tablet herein is an effective amount and is typically that amount which provides a minimum effective coverage of the exterior surface area of the tablet, although this invention also encompasses those instances where there is partial coverage of the exterior surface as well.

If desired, one or more layers of gellan gum coating may be employed using this invention. Those of skill in the art will be able to determine the extent of any layering depending on the drug, tablet size, and its physical and chemical and therapeutic properties and characteristics from a reading of this specification and using their skill in the art.

It is preferred that coating be continuous or nearly continuous over the surface of the tablet although an interior coating may be achieved. An effective depth of coating is provided for retention. It is also desired that the tablet coatings herein be somewhat resilient with respect to handling, to peeling and to flaking and being rubbed off the coated tablet.

As referred to above, application of the gellan gum aqueous composition as a coating to the tablet is preferably carried out by placing a tablet capable of receiving and adhering a gellan gum tablet coating composition of this invention in any acceptable coating application system. An acceptable coating application system is illustratively any system which has the capability to apply a gellan gum coating composition of this invention to a tablet to provide an effectively, preferably uniformly coated tablet. For example, an acceptable coating application system includes without limitation, a plain fluid bed system (i.e., one without any "Wurster" type insert), including a fluid bed spray tower of any reasonable size and design and systems similar thereto in function and utility.

Air Suspension Coating systems useful here as an illustrative application system include those described in Ullman's Encyclopedia of Industrial Chemicals, Volume A16 pages 583–584 (1990) which includes a description of the Wurster process. Ullman's Encyclopedia of Industrial Chemicals, Volume A16 pages 583–584 (1990–1996) is incorporated herein by reference in its entirety. This incorporation includes the chapter Microencapsulation authored by Christopher A. Finch of Pentafin Associates, Weston Turville, AYLESBURY HP 22 5TT, UK. Also, acceptable for use to prepare coated tablets of this invention are illustratively a variety of side vented coating pans, spray dryer(s), continuous coating pans, and conventional coating pans, such as those with systems for mechanically providing the gellan gum composition to a tablet in an effective manner using mechanical means as for example by spray nozzles or the like. Also acceptable as a spray tower system is a conventional fluid bed tower equipped with a suitable spray apparatus. Any application system capable of applying a composition of this invention to a tablet is an acceptable system for coating tablets employing the-aqueous gellan gum coating composition of this invention. As the coating system is not critical, any size coating system is acceptable. Batch and continuous processes, semi-continuous and suitable variations thereof are envisioned without limitation.

The "Wurster" type fluid bed dryer typically comprises a cylindrical outer vessel having a perforated floor through which a heated gas passes upwardly to heat and fluidize a batch of tablets or particles fed to or formal therein. A concentric, open ended inner cylinder is suspended above the center of the perforated floor of the outer vessel. A spray nozzle, or projecting part, centered beneath the inner cylinder sprays a solution of the coating material. upwardly into the inner cylinder as the fluidized materials pass upwardly through the spray in the inner cylinder. The particles circulate upwardly though the center of the inner cylinder and downwardly between the inner and outer cylinder. The air that fluidizes the particles also serves to vaporize the water causing the composition to deposit as a film or coating onto the surface of each particle. After repeated passes through the coating zone in the inner cylinder, a sufficient thickness of polymer accumulates and coalesces over the entire surface of each particle as to coat each particle. A description of an acceptable "Wurster" type fluid bed dryer is found in J. Am Phar. Assoc., Sci. Ed. Vol. 48, (1959) Air Suspension Technique of Coating Drug Particles by Wurster, Dale E. and Preparation of Compressed Tablet Granulations by the Air Suspension Technique II, Wurster, Dale E, Sci. Ed. Vol. 49 (1960) both of which are incorporated herein in their entirety by reference. In operation of the dryer, the operator will typically have the tablets discharged when the desired amount of coating has been applied to the tablets. This is generally based on the amount of coating composition sprayed in the dryer from which based on prior experience, the amount of weight gain (%) of the tablets during coating can be determined. Electronic or equivalent controls are typically installed on the dryer to regulate the process such as regulating the temperature of the inlet air and the amount of such inlet air and its pressure.

In side vented coating pan systems, as the material inside is coated it increases in size and weight. Generally the materials to be coated accumulate adjacent an end wall and along a side wall of the drum in the system. As the drum rotates, the material is tumbled and is coated with a coating composition from one or more spray nozzles. Initially the material may form a mass and as the material is sprayed and increased in size the large particles migrate away from the end wall and cannot penetrate the mass of smaller particle adjacent the end wall. Eventually, substantially all of the material is uniformly coated a such that the material forms a new mass wherein the particles are slightly larger than the original mass formed by the uncoated particles. The process repeats itself such that the particles are coated with additional composition from the spray nozzle, thereby again increasing in size and weight and migrating away form the end wall. The cycle continues until the particle achieve a desired uniform size.

Particularly useful self contained side vented coating pan system in this invention are available under the Accela Cota brand sold by Thomas Engineering Incorporated, 575 West Central Road, Hoffman Estates, Ill., 60195–0198, U.S.A. Various size pans may be satisfactorily employed herein and include without limitation 15, 24, 48 and 60 inch pans, if desired. The size of the pan and dryer are not critical. The Compu Lab model sold under the Accela Cota brand works well for laboratory size charge (feed) quantities. Those of skill in the art will recognize that various size pans may be employed depending on the amount of materials to be coated and other coating operations.

The Accela Cota brand side vented coating pan system comprises a rotating drum and as the drum is rotated containing the tablets to be coated, the coating composition is applied to the tablets by means of one or more nozzles positioned within the rotating drum so as to direct the coating composition to the tablets in the bed. As the pan is rotated and the coating composition is further applied to the tablets, the tablets achieve a desired coating. This apparatus is also a dryer for substantially drying the tablets as the tablets are coated. The side wall of the drum is perforated and a flow of air is provided into the drum through apertures for drying the coating composition on the tablets. A system is also provided on the apparatus for removing the outlet air and for removing the coated tablets.

The nozzles of this side vented coating system are preferably adjustable and may be positioned nearer to and closer to the bed of tablets to be coated depending on the conditions of use and the desired coating composition quality and quantity, among other factors. Those of skill in the art will recognize that the distance of the nozzle or nozzles from the bed is important and may be adjusted to provide optimum coating compositions. In operation such nozzle placement distances will be an effective distance and will be selected from a plurality of available positions and will depend on the tablets being coated, the coating compositions, the degree of coating desired and other conditions of the particular coating operation, among other factors.

Those of skill in the art will recognize that one or more nozzles may be employed as desired to provide optimum coating. The number of nozzles is not critical and may be varied as needed depending on the coating operation and other factors. The nozzle throat diameter is typically from about 0.028 inch to about 0.100 inch although, greater and smaller throat diameters may be employed. A nozzle throat diameter of somewhere about 0.040 inch is preferred although that size is not critical. The nozzle(s) is preferably aimed perpendicularly or nearly perpendicular to the bed although other direction(s) of aim may be employed if desired. Those of skill in the art will recognize that the pan may be rotated at a speed selected from a plurality of operating speeds. The pan may be stopped after the material has been coated and the matter removed.

In general, an effective nozzle distance for applying a coating to a tablet using a side vented pan coating system is in the range from being positioned less than about a ¼ inch from the bed to about 15 inches and preferably from about 8 to about 12 inches although greater of lesser nozzle distances may be employed if desired depending on the weight of tablets charged into the pan and coating system composition and other factors such as temperatures, spray rate and air volumes.

If desired, the same or a similar coating application system can be employed for both a first and a second or sequential coating applications or different coating application systems may be employed for a first or second or more coating applications. If desired, the same coating application system can be used to apply a first and second or more coatings with or without removal of the tablets from such a system between the first and second or more coatings.

The gellan gum coated tablets of this invention as afore-described or such actives including but not limited to aspirin, naproxen sodium, acetaminophen, ibuprofen, celecoxib, oxaprozin, sildenafil citrate, alendronate sodium, mixtures thereof and the like and other medicines may be internally consumed by humans and animals in a typical customary manner and may be prepared as afore-described with respect to aspirin and tablets in preceding pages of this application.

While illustrative useful application systems have been described herein, those of skill in the art will recognize that such description is provided to provide information as to the possible application and use herein in accordance with this invention. Those of skill in the art will recognize that the actual operation of any such application system will vary and may be varied from "text book" type description of such operation in according with the parameters and conditions of any desired operation, among other factors. Configurational and design changes may be made on such applications systems and operating parameters may be varied.

EXAMPLES

Examples 1–17 and Examples A and B herein, are provided to merely illustrate the preparation of acceptable coated tablets in accordance with this invention and are provided by way of illustration and are not intended to limit the invention in any way. All percents and any parts are by weight unless otherwise indicated. These Examples 1–17 and A and B illustrates the practice of this invention in a non limiting fashion. Various application systems including fluidized feed systems and pan vented coated systems are illustrated without limitation.

Example 1

An acceptable high gloss gellan gum coated (red colored) tablet was prepared in this Example in accordance with this invention.

A gellan gum composition useful for coating tablets was prepared comprising 30 grams gellan gum, 1968 grams deionized water and two grams sodium citrate to provide a 1.5% by weight gellan gum aqueous composition useful for coating tablets.

This aqueous gellan gum composition was prepared by weighing the deionized water into a clean dry residue free beaker and weighing out the gellan gum (Kelcogel) and sodium citrate. The water was then mixed with a laboratory mixer to create a vortex. The gellan gum powder and sodium citrate was slowly introduced into the vortex to achieve dispersion. Stirring was continued without heat to finalize the dispersion of gellan gum. Heat was applied while stirring until the dispersion temperature was about 70° C. to hydrate the gellan gum. Care was taken to avoid charring the resulting dispersion, i.e. employing sufficient stirring and avoiding overheating. The beaker was removed from the stir plate and cooled to ambient temperature to make the gellan gum aqueous composition available for coating.

The tablets to be coated herein were uncoated placebos (½ inch, standard concave shape, 390 mg. weight each).

A hydroxypropylmethylcellulose (HPMC) and color composition having the ingredients shown in Table 1 below was applied to these uncoated placebos to prepare a tablet which had color and appearance mimicking recognized commercial products using a Compu Lab side vented 15 inch coating pan system as an application system.

| Ingredients: | Weight (g) |
| --- | --- |
| Pharmacoat 606 (10%) | 1800 |
| D-447 | 90 |
| TA | 30 |
| Water | 130 |
| Total Weight | 2050 grams |
| Red (D447) (Dye Dispersion) | |
| 11.83% Titanium Dioxide | 23.64 grams |
| 20.01% FD&C Red No. 40, Hi Dye Lake | 40 grams |
| 8.18% FD&C Yellow No. 6 dye | 16.36 grams |
| 2.0% EDTA solution (40%) | 4 grams |
| 57.98% Distilled Water | 115.91 grams |
| | 199.91 grams |

Pharmacoat 606 (10%) = hydroxypropyl methyl cellulose
TA = triacetin (plasticizer)

The side vented pan coating system used herein employed one nozzle which was aimed more or less directly at the bed of tablets to be coated and was positioned at a acceptable standard distance from the outer portion of that bed. That nozzle had a throat diameter of about 0.040 inch. Operating data was such that 466 grams of coating solution was applied in under 35 minutes. Inlet temperatures were between 60° F. and 75° F. and the outlet temperatures were between 45° F. and 50° F. Pan RPMs were about 10.

These placebos (red colored) were then coated with the gellan gum aqueous composition (prepared in a first step of this Example) in the same 15 inch diameter pan Compu Lab side vented coating system as an application system.

The parameters for coating the red tablets with gellan were such that about 800 grams of solution was applied in just over one hour. Inlet temperatures ranged from 55° F. to 65° F.

This application system employed one nozzle positioned in close proximity to the tablet bed and aimed at the bed of tablets to be coated. This produced an acceptable high gloss gellan gum coated placebo.

Samples were taken after weight gains of 0.05, 0.1, 0.2, 0.3, 0.4, 0.5, 0.6 and 0.7% respectively to document and monitor coating appearance and character. Further, this Example provided acceptable tablets with very high gloss and lubricious mouthfeel. This Example demonstrates the gloss and mouthfeel attributes of the gellan gum coating of this invention and also demonstrates the compatibility of clear gellan gum coating with a base coating of polymer and lake color system and aspartame. Tablets of this Example had a gloss better than the gloss of commercially available sugar coated products.

Example 2

In a first step, an acceptable gellan gum aqueous coating composition was prepared according to Example 1.

The tablets to be coated herein comprised uncoated placebos (⅜ inch, rounded shape, 355 mg. weigh each, standard concave shape). These uncoated placebos were first coated with a polymer/color composition comprising:

| Ingredients: | Weight (g) |
| --- | --- |
| 606 (10%) | 2000 |
| SS-1092 | 125 |
| TA | 33 |
| Water | 200 |
| Total Weight | 2358 g |
| Brown (SS-1092) (40% solids): | |
| 37.2% Titanium Dioxide | 37.2 grams |
| 2.65% FD & C Yellow No. 6 Low dye Lake | 2.65 grams |
| 0.15% Red Iron Oxide | 0.15 grams |
| 2.0% EDTA solution (40%) | 2.00 grams |
| 58.0% Distilled Water | 58.00 grams |
| | 100.00 grams |

SS = Spectrablends, from Warner Jenkinson*

This coating operation was carried out in a Compu Lab 15 inch side vented coating system in a manner similar to that employed for the color coating in Example 1, above.

These once coated placebos were then charged into a Compu Lab 15" pan side vented coating system wherein a gellan gum coated high gloss tablet was prepared. One nozzle was employed which was positioned in close proximity to the bed of tablets to be coated.

Operating data was such that 762 grams of gellan solution was sprayed in about 35 minutes. Temperatures and other parameters were similar to those in example 1.

Samples were taken after weight gains of 0.1, 0.2, 0.3, 0.4, 0.5 and 0.6% respectively to monitor coating character. This Example provided acceptable tablets of this invention with high gloss and lubricious mouthfeel. This Example demonstrates the compatibility of clear gellan gum coating with polymer/oxide color systems in the base coat.

Example 3

High gloss gellan gum coated tablets were prepared by preparing in a first step a gellan gum composition as described in Example 1 above which contained 1.5% Kelcogel and 0.175% aspartame.

The tablets to be coated herein comprised uncoated placebos which were coated with a polymer/color composition comprising:

| Ingredients: | Weight (g) |
|---|---|
| 606 (10%) | 600 |
| D452 (40%) | 24 |
| PEG460 | 12 |
| Water | 42 |
| Total Weight | 678 |
| Red (D452) (Dye Dispersion) | |
| 12.0% Titanium Dioxide | 420 grams |
| 20.0% FD&C Blue 1, Hi Dye Lake | 700 grams |
| 2.00% FD&C Yellow No. 6 dye | 70 grams |
| 6.0% FD&C Red No. 40 dye | 210 grams |
| 2.5% EDTA solution (40%) | 87.5 grams |
| 57.5% Distilled Water | 2012.5 grams |
| | 3500 grams |

The application was carried out in a Compu Lab side vented coating 15" pan. Processing parameters were similar to parameters in Example 1 and Example 2.

The once coated placebo from Step A above was then coated with a gellan gum aqueous composition with aspartame added in a Compu Lab side vented coating 15" pan in a Step B. Processing parameters were similar to those in Example 1 and Example 2.

A sweet tasting, high gloss, acceptable coating was produced.

Samples were taken after weight gains of 0.1, 0.2, 0.3, 0.4 and 0.5% respectively to monitor coating character. Acceptable tablets were prepared in this Example which had high gloss and lubricious mouthfeel. This demonstrates the compatibility of clear gellan gum coating with polymer/dye color systems in the base coat as well as aspartame compatibility in the exterior coating.

Example 4

An acceptable tablet coating composition comprising a gellan gum composition was first prepared according to Example 1.

The tablets to be coated herein comprised uncoated active drug ingredient tablets of about 400 milligram (mg.) weight each:

| Ingredients: | Weight (g) |
|---|---|
| Pharmacoat 606 (10%) | 100 |
| D-947 | 4 |
| TA | 2 |
| Water | 42 |
| Total Weight | 148 |
| Pink (D947) (Dye Dispersion) | |
| 37.6% Titanium Dioxide | 47 grams |
| 2.4% D & C Red No. 27 dye | 3 grams |
| 1.6% EDTA solution (40%) | 2 grams |
| 58.4% Distilled Water | 73 grams |
| | 125 grams |

TA = triacitin

A fluidized bed dryer system ("Wurster" type) was employed to carry out a first coating of these initially uncoated tablets. The fluidized bed system comprised a 4 inch circular plexiglass column having a perforated base plate with about 150 holes each about ⅛" diameter therein and having positioned in this base plate, a liquid spray nozzle which protruded about ¼ inch in the interior of the column above the base plate. The spray nozzle had a 0.035 inch diameter throat and was connected externally to a coating solution supply system. An air supply system was connected to the base plate and an air outlet filter positioned atop the column provided for the air outlet. The air supply system had a temperature regulator system on it. In operation the tablets to be coated were charged to this fluid bed dryer, compressed air was forced into and through the base plate and color coating composition was sprayed by the spray nozzle into the bed of tablets from the coating solution supply system. 20 grams of polymer solution was sprayed in less than 10 minutes with an outlet temperature at about 120° F.

An acceptable high gloss tablet was then prepared by coating over the color coated tablets prepared immediately above in the same fluidized bed dryer as described above by applying the previously made gellan gum coating composition of this Example to the color coated tablets. In this coated active product tablet, the color coat was the first coating (primary, initial, or base) and gellan gum was the second coating or overcoating.

Processing parameters were such that about 180 grams of gellan gum solution were sprayed in under 20 minutes with a processing temperature around 120° F. This demonstrates gellan dye coating compatibility.

Example 5

An acceptable gellan gum coating composition was prepared according to Example 1.

The tablets to be coated herein comprised active ingredient tablets of about 476 mg weight each, which was first coated with a polymer/color coating composition comprising:

| Ingredient | Weight |
|---|---|
| 606 (10%) | 100.0 |
| D-452 (40%) | 4.0 |
| PEG 400 | 2.0 |
| Water | 7.0 |
| Total Weight | 113.0 g |
| Red (D452) (Dye Dispersion) | |
| 12.0% Titanium Dioxide | 420 grams |
| 20.0% FD&C Blue 1, Hi Dye Lake | 700 grams |
| 2.00% FD&C Yellow No. 6 dye | 70 grams |
| 6.0% FD&C Red No. 40 dye | 210 grams |
| 2.5% EDTA solution (40%) | 87.5 grams |
| 57.5% Distilled Water | 2012.5 grams |
| | 3500 grams |

This first coating was carried out in a fluidized bed dryer as described in Example 4. Processing parameter allowed about 110 grams to be sprayed in less than 11 minutes. Temperatures were similar to those of Example 4.

In a second step of this Example 5, a high gloss gellan gum coated tablet was prepared by coating the once coated tablet prepared immediately above in a fluidized bed dryer as described above with a gellan gum composition.

Processing parameters allowed 200 grams of gellan gum solution to be applied in about 22 minutes with temperatures similar to those in Example 4.

Tablets produced in this Example were acceptable and had high gloss and lubricious mouthfeel. These tablets were essentially the same as the acceptable tablets produced in the previous Example.

Example 6

Application of a Clear Gellan Gum Coating to an Uncoated Tablet

Purpose: To apply clear coating of an aqueous gellan gum composition to uncoated uncolored tablets to provide an acceptable high gloss coated tablet of this invention.

Method: Using a 1.5% gellan gum solution useful for coating tablets

| % | Grams |
|---|---|
| 1.5% Gellan Gum | 22.5 grams |
| 0.10% Sodium Citrate** | 1.5 grams |
| 98.4% Deionized Water | 1476.0 grams |
| | 1500 grams |

**Dihydrate, powder

Using a suitable mixing blade and mixer, with good vortex the gellan gum was slowly added to water. Once the gellan gum was dispersed sodium citrate was added and heating initiated. Heat to 70° C. Allow solution to cool and form gel.

Coating procedure: Spray 200 grams of 1.5% gellan solution (room temperature) onto 420 grams uncolored active ingredient tablets using a laboratory fluidized column (similar in concept to an Aeromatic Strea 1). Samples of tablets were taken at 0.05, 0.1, 0.2, 0.3, 0.4 and 0.5% weight gains respectfully.

Processing parameters were such that 200 grams of gellan gum solution were applied in under 20 minutes. Inlet temperatures were between 160° F. and 180° F. Outlet temperatures were between 115° F. and 125° F.

In this Example, acceptable tablets were produced which had very high gloss and lubricious mouthfeel. This Example demonstrates that gellan gum coating of this invention can be successfully coated onto a tablet absent a base coating on that tablet.

The resulting gloss was judged superior to commercially available clear coatings (non gellan gum) and commercially available sugar coatings.

Example 7

Preparation and evaluation of the viscosity of 1.8% and 2.0% gellan gum composition to be measured for viscosity over a temperature range of about room temperature to about 60° C. and also to be coated onto color coated tablets.

These solutions of gellan gum were sprayed onto color coated tablets at temperatures between 24° C. and 30° C. (with viscosities ranging from +28,000 cps to 55,000 cps).

Materials: Gellan Gum
Deionized Water
Na Citrate
Procedure: A 1.8% gellan and a 2% gellan solution were made as Example 1

| 1.8% | | |
|---|---|---|
| Gellan Gum | 1.8% | 27.9 g |
| Deionized Water | 98.08% | 1471.2 g |
| Na Citrate | 0.12% | 1.8 g |
| TOTAL | | 1500 g |
| 2.0% | | |
| Gellan Gum | 2.0% | 30.0 g |
| Deionized Water | 97.87% | 1468.05 g |
| Na Citrate | 0.13% | 1.95 g |
| TOTAL | | 1500 g |

Viscosity Measurements
Spindle=3, Vessel=600 ml beaker, DV-I+Brookfield Viscometer, Viscosity was measured while solutions cooled.

| Temp. °C. | Viscosity (cp) | Speed RPM |
|---|---|---|
| 1.8% by wt. RGellan Gum | | |
| — | — | — |
| 60 | 44 | 100 |
| 50 | 60 | 100 |
| 40 | 127 | 100 |
| 35 | 2200 | 50 |
| *30 | 28460 | 2.5 |
| **25 | 38730 | 2.5 |
| — | 2.0% by wt. Gellan Gum | — |
| — | — | — |
| 48 | 89 | 100 |
| 40 | 164 | 100 |
| 34.6 | 17680 | 5 |
| 30 | 39740 | 2.5 |
| *28 | 45600 | 2.0 |
| **24.6 | 55440 | 2.0 |

Key:
*Viscosity measured before start of coating application to tablets
**Viscosity measured after coating application was completed to tablets 1.8% Gellan gum
Brookfield Engineering Laboratories, Inc., 240 Cushing Street, Stoughton, Mass. 02072–2398 U.S.
Processing parameters were such that 200 grams of gellan gum solution was applied in about 16 minutes with temperatures similar to those in previous example. The temperature of 1.8% Gellan at end of run was 26.0° C.
2% Gellan Gum
Application as a coating to a tablet using a fluid bed dryer took under 16 minutes with 200 grams of gellan gum solution applied. Processing parameters were similar to previous example.

There was no problem spraying an aqueous gellan gum composition at 1.8% or 2.0% at room temperature at a viscosity ranges between about 28,460 cps at about 55,500 cps using conventional peristaltic pumping and standard nozzle apparatus.

Samples were taken after weight gains of 0.05, 0.1, 0.2, 0.3, 0.4 and 0.5% respectively to monitor coating character. In this Example, acceptable tablets were produced having high gloss and lubricious mouthfeel. This Example showed that gellan gum aqueous coating compositions can be successfully employed according to this invention at 1.5%, 1.8% and 2.0% solids. Gloss and mouthfeel are not compromised when applying (via spraying) higher solids coating compositions.

Example 8

Preparation of a 1.8% by weight and 2.0% by weight aqueous gellan solution to be used for spraying a clear coating of gellan gum onto a color coated tablet. The gellan gum solutions will be sprayed at an elevated temperature.
Materials: Gellan Gum
Deionized Water
Na Citrate
Procedure: Solutions were made:

| 1.8% Gellan Solution (1 L) Prepared | | |
|---|---|---|
| Gellan Gum | 1.8% | 18.0 g |
| Deionized Water | 98.08% | 980.8 g |
| Na Citrate | 0.12% | 1.2 g |
| TOTAL | | 1000 g |
| 2.0% Gellan Solution (2 L) Prepared | | |
| Gellan Gum | 2.0% | 40 g |
| Deionized Water | 97.87% | 1957.4 g |
| Na Citrate | 0.13% | 2.6 g |
| TOTAL | | 2000 g |

Prepared gellan solutions (1.8% concentration and 2.0% concentration) were then sprayed onto tablets using the fluid bed coating equipment. The solution were sprayed at 40° C. where viscosity of each solution is below 200 cps.

Processing parameters for gellan gum solution (1.8% solids) allowed about 170 grams of solution to be applied in under 20 minutes. Processing temperatures were similar to previous example.

Processing parameters for gellan gum solution (2.0% solids) allowed for 150 grams of solution to be applied in about 17 minutes. Processing temperatures were similar to previous examples.

Heating the solution to lower viscosity had no detrimental effect on the coating delivered to the tablets. Spraying at elevated temperatures allows for high solids at lower viscosity and delivers a film comparable to lower solid solutions sprayed at room temperature.

Example 9

Gellan with pigment sprayed onto tablets. Pigment addition to gellan coating solutions at room temperature is difficult due to viscosity of gellan solution. Pigment is easily dispersed, however, when gellan coating solution is heated to 40° C. or above. At this temperature the coating solution is fluid (viscosity below 200 cps) and dispersion of pigments in gellan solution is easily achieved with a standard laboratory mixer.

Gellan solution: Follow procedure recited in Example 1.
Formula:

| 1.5% Gellan gum | 45 grams |
|---|---|
| 0.1% Sodium Citrate | 3 grams |
| 98.4% Deionized Water | 2952 grams |

Sodium Citrate (a sequestrant)

1000 grams of above gellan coating solution (1.5% gellan) is held at 40° C. To this preparation is added 3.0 grams Propylene Glycol and 3.0 grams of Lecithin (Alcolec F-100) while mixing. The color component (7.5 grams of Green—Spectra Spray SS-1091) is added but while mixing and holding solution temperature at 40° C. or above. Mix until homogenous.

Grams of gellan/color preparation from above was then sprayed onto 420 grams of tablets in a fluidized bed coating apparatus. The 420 grams of tablets is a combination of 25 grams of tablets with active ingredients and 395 grams of placebo tablets. Samples of tablets were taken at 0.5, 1.0, 2.0, 2.5 and 3.0% weight gains respectively.

Tablets prepared in this Example had high gloss, uniform color and lubricious mouthfeel. This Example demonstrates the compatibility of gellan gum with lake color system for aqueous film coating.

Example 10

Gellan Clear Coating Sprayed on Gellan/color Coated Tablets From Example

Tablets from Example 9 which were coated with gellan and color coating solution (gellan, Green Spectra-Spray, Propylene Glycol and Lecithin) were taken and coated again with a clear gellan coating solution also sprayed at 40° C. (1.5% gellan). This demonstrates the compatibility of gellan/color coating with gellan when used as a top coating or gloss coat. The top coating of clear gellan was applied at 40° C. with a total weight gain of 0.5%. Samples were taken. at 0.05%, 0.1%, 0.2%, 0.3%, 0.4% and 0.5% with gloss increasing with each additional weight gain of clear coating.

Tablets prepared in this Example had a higher gloss than the tablets of Example 9. These tablets also had a lubricious mouthfeel. This Example demonstrates the ability of this invention to improve tablet gloss when using clear gellan gum coating as an overcoat or as a gloss coating. This Example also demonstrates the compatibility of gellan gum coating with a base coat comprising gellan gum and lake color. Coated tablets produced herein have gloss and appearance which is better than or equivalent to commercially manufactured sugar coated tablets.

Example 11

Gellan Gum With Pigment (Oxides)

Using 1.5% gellan gum solution prepared in example 11, maintain gellan solution at 40° C. and add color/plasticizer system as in example 10.
Color system added to 1000 gram gellan solution:
3.0 grams Lecithin (Alcolec F-100)
3.0 grams propylene glycol
7.5 grams Oxide (Spectra Spray 1092)
Pigment disperses easily in gellan solution at 40° C. because of low viscosity of heated solution.

760.1 grams of gellan/oxide preparation were sprayed at 40° C. onto 420 grams of tablets in a fluidized columns (similar to Aeromatic Strea 1). Samples were taken at 0.05%, 0.1%, 0.2%, 0.3%, 0.4% and 0.5% weight gains.

Tablets were produced in this Example that had high gloss, uniform color and lubricious mouthfeel. This Example demonstrates the compatibility of gellan gum with lake color systems and plasticizer in aqueous film coating systems.

Example 12

Gellan Gum Coating on Vitamin Tablets and Placebos

Purpose: To apply clear coating of Gellan gum solution to colored vitamin tablets to demonstrate that acceptable gloss can be obtained.

Method: Using a 1.5% Gellan solution:
1500 grams total:

| %                    | Grams        |
|----------------------|--------------|
| 1.5% Gellan Gum      | 22.5 grams   |
| 0.10% Sodium Citrate**| 1.5 grams   |
| 98.4% Deionized Water | 1476 grams  |

**Dihydrate, powder

Mixing Instructions: Follow procedure recited in Example 1.
Coating Instructions: Follow procedure recited in Example 4 (sprayed at room temperature).

Tablets used totaled 420 grams (210 grams peach colored vitamins and 210 grams of uncoated placebo tablets)

In this Example, acceptable tablets were also produced which result in vitamin tablets and placebo tablets that had a high gloss and lubricious mouthfeel. This Example demonstrates that gellan gum applied as a clear aqueous coating in accordance with this invention is compatible with vitamins and placebo tablets and results in tablets having an improved gloss and mouthfeel over the uncoated tablets.

Example 13

Gellan Gum Coating on Vitamin Tablets and Placebos Sprayed at 40° C.

Purpose: To apply clear coating of Gellan gum solution to colored vitamin tablets to determine if appropriate gloss can be obtained.
Method: Using a 1.5% Gellan solution:
1500 grams total:

| %                    | Grams         |
|----------------------|---------------|
| 1.5% Gellan Gum      | 22.5 grams    |
| 0.10% Sodium Citrate**| 1.5 grams    |
| 98.4% Deionized Water | 1470.0 grams |

**Dihydrate, powder

Mixing Instructions: Follow procedure recited in Example 1.
Coating Instructions: Follow procedure recited in Example 1 (sprayed at 40° C.).

Tablets used totaled 420 grams (210 grams peach colored vitamins and 210 grams of uncoated placebo tablets)

In this Example, acceptable vitamin coated tablets were produced in accordance with this invention which had high gloss and lubricious mouthfeel comparable to the tablets from Example 12. This Example demonstrates that ability of gellan gum to be processed in accordance with this invention at elevated temperatures with no negative impact on gloss or mouthfeel of the coated tablets.

Example 14

Gellan Gum With Pigment: Lake With PEG 400 Increased*

*Rather than 20% PEG 400 of total gellan gum solids, 50% PEG 400 of gellan solids will be evaluated
Gellan solution preparation: Follow procedure recited in Example 1.
Mixing instructions: Follow procedure recited in Example 1.
Coating Preparation
600 grams 1.5% Gellan solution (heated to 40° C.)
4.5 grams Peach (SS-1094)
4.5 grams PEG 400
  Peach (SS-1094) (40% solids)
  37.2% titanium dioxide 37.2 grams
  2.65% FD&C yellow no.6 low dye lake
  0.15% red iron oxide 0.15 grams
  2.0% EDTA solution (40%) 2.00 grams
  58.0% distilled water 58.00 grams Spray 581.5 grams of above formula (40° C.) onto 420 grams placebos using a fluidized column (similar in concept to an Aeromatic Strea 1). Samples of tablets taken at 0.5, 1.0, 1.5, 2.05 weight gains.

This resulted in improved and acceptable film flexibility, improved gloss and good tablet coverage. This Example results in acceptable tablets with high gloss and lubricious mouthfeel. This Example demonstrates the compatibility of gellan gum with lake color systems and plasticizer at elevated concentrations. The elevated plasticizer level enables greater film flexibility.

Example 15

Gellan Gum With Pigment: White Formula

*Gellan solution preparation: Used 1000 grams from solution made above, which had cooled to around 40° C.
Coating Preparation
1000 grams 1.5% gellan solution
9.4 grams White (SS-1031) (50% solids)
3.0 grams Propylene Glycol
3.0 grams Lecithin (Alcolec F-100)
  White (SS-1031) (50%) solids
  25% titanium dioxide 50 grams
  25% talc 50 grams
  2.5% EDTA solution (40%) 5 grams
  47.5% distilled water 95 grams Weigh gellan solution into appropriate beaker (37.5° C.). Add Propylene Glycol and lecithin. Stir, with an appropriate stirrer until it is mixed well. Add white dispersion. Keep temperature around 40° C. prior to spraying. Combined at this temperature, pigment dispersed easily and mixed into the gellan solution with no problems.

Coating trial: Spray 711.2 grams of above formula (40° C.) 420 grams placebos* using a fluidized column (similar in concept to Aeromatic Strea 1). Samples of tablets taken at 0.5, 1.0, 1.5, 2.0, 2.5, 3.0% weight gains.
*25 grams active tablets part of charge The Example produced acceptable tablets that had good lubricious mouthfeel and gloss characteristics that are higher than commercially available white coating systems. This Example demonstrates that gellan gum is compatible with titanium based color systems and plasticizers. This Example also demonstrates gellan gums ability to impart gloss in the presence of these ingredients.

Example 16

Gellan Gum With Pigment: Lake (With HPMC Addition)

Using 1.5% gellan solution prepared above.
Coating preparation:
1000 grams 1.5% gellan solution
7.5 grams Green (SS-1091)

3.0 grams Hydroxypropylmethylcellulose (Pharmacoat 606)
3.0 grams PEG 400
where PEG =polyethylene glycol 400 and

| Green (SS-1091) comprised: | |
|---|---|
| 38.4% titanium dioxide | 76.8 grams |
| 2.65% FD&C yellow No. 610 W dye lake | 2.65 grams |
| 0.15% red iron oxide | 0.15 grams |
| 2.0% EDTA solution (40%) | 2.00 grams |
| 58.0% distilled water 58.00 grams for a total of | 200 grams |

Weigh gellan solution into appropriate beaker and heat. Add PEG 400 and HPMC (temperature when added=60° C.). Mix with an appropriate stirrer until dissolved. Add lake dispersion until it is mixed well.

Coating trial: Spray 760.1 grams of above formula (40° C.) 420 grams placebos* using a fluidized column (similar in concept to an Aeromatic Strea 1). Samples of tablets taken at 0.5, 1.0, 1.5, 2.0, 2.5, 3.0% weight gains.

*25 grams active tablets as part of charge (charge is the tablets to be coated which are provided to the fluidized column)

Results: Tablets coated to a 3% weight gain; addition of HPMC improved film flexibility and enabled formulae to be made with PEG added at a standard level (20% of gellan solids level); gloss was not compromised. This Example further resulted in acceptable tablets with a higher gloss than tablets coated with HPMC alone. Also, the tablets of this Example prepared in accordance with this invention, had the lubricious mouthfeel characteristic of gellan gum coatings. Further, this Example demonstrated the compatibility of gellan gum with HPMC.

Example 17

Gellan Gum Coating Solution With Dye Dispersion

A tablet coating composition comprised of a gellan gum composition was first prepared (1.5% gellan concentration) according to Example 1. Tablets (420 grams) were coated using a fluidized column (similar in concept to an Aeromatic Strea 1). These tablets were coated with a polymer/color coating composition and the gel gum solution which were combined as follows:

1000 grams 1.5% gellan solution
3.75 grams Green dye dispersion (D412)
3.0 grams Propylene Glycol
3.0 grams Lecithin (Alcolec F-100)

Weigh the gellan into a beaker and add the propylene glycol and lecithin while gellan preparation in +40° C. Once the propylene glycol and lecithin are dispersed, add the dye dispersion. 807.8 grams of above formula were sprayed onto 420 grams of tablets (395 grams of placebos and 25 grams of tablets with active drug substance).

This Example provided acceptable tablets with very high gloss and lubricious mouthfeel. This Example further demonstrates the compatibility of gellan gum with dye color systems and plasticizer.

A number of active ingredients were coated in accordance with this invention. These actives included:

Example A

| Active: | Weight gain (%): |
|---|---|
| Acetaminophen (500 mg tablet) | 0.22% |
| Acetaminophen (325 mg tablet) | 0.22% |
| Acetaminophen (500 mg caplet) | 0.30% |
| Aspirin (325 mg) | 0.20% |
| buffered aspirin (325 mg tablet) | 0.25% |
| acetaminophen, aspirin and caffeine (650 mg tablet) | 0.20% |
| acetaminophen, aspirin and caffeine (650 mg caplet) | 0.20% |
| aspirin (432 mg tablet) | 0.20% |
| ibuprofen (200 mg tablet) | 0.30% |
| ibuprofen (200 mg tablet) | 0.30% |
| ibuprofen (200 mg tablet) | 0.20% |
| naparoxyn sodium (220 mg tablet) | 0.23% |

The weight gain of gellan gum provided onto the respective table is shown in the right hand column as a % of the total coated tablet weight.

| Coating Procedure: | | |
|---|---|---|
| Gellan formula used: | % | wt (g) |
| Gellan | 1.5 | 18 |
| Sodium Citrate | 0.1 | 1.2 |
| Methylparaben | 0.1 | 1.2 |
| Epikuron 100 P1 | 0.45 | 5.4 |
| PEG 400 | 0.15 | 1.8 |
| DI H$_2$O | 97.7 | 1172.4 |
| | | 1200 Total |

Charge: 2 kg total, mostly consisted of ⅜" concave placebos, uncoated, with several bottles of over the counter pain tablets added to the placebos.

Equipment: 15" pan using Thomas Accela-Cota (Compu-Lab)

Results

All of the coatings produced exceptional gloss (with gloss numbers showing a minimum of 14% increase in gloss with several coatings resulting in a 99% increase in the gloss). Gloss analysis performed on TriCor Systems Inc. Surface Analysis System, Model #805A. Mouth feel also enhanced using gellan gum. Disintegration times tested on the national brands and gellan coated samples in dissolution media listed in USP and, in some cases, in SGF (simulated gastric fluid).

Example B

Process Work

Evaluation of process that utilizes varying concentrations of gellan gum solution during a single pan run. The process was evaluated to try and take advantage of both reduced spray times of the higher concentration solutions as well as improved gloss of the lower concentration gellan gum solutions.

Procedure

All runs preformed on Thomas Engineering's Compu-Lab side-vented 15" pan.

Placebo run charge=1900 grams placebo.

Active run charge=35 grams of various brand name and generic ibuprofen tablets and caplets. 1865 grams placebo, 1900 grams total.

Placebo=⅜" standard concave placebo, coated with HPMC red to a 3.0% weight gain-refer to prior example of gellan patent for procedure and dye formulation.

Example 1B

Summary

1.5% Gellan Solution

| | | |
|---|---|---|
| 1.50% | 18.0 grams | Gellan Gum (Kelco L/N 68014a) |
| 0.10% | 1.2 grams | Sodium Citrate (JT Baker) |
| 0.10% | 1.2 grams | Methyl Paraben (Spectrum) |
| 0.45% | 5.4 grams | Lecithin (Epikuron 100P1, Lucas Meyer Inc.) |
| 0.15% | 1.8 grams | Polyethylene Glycol 400 (Spectrum) |
| 97.70% | 1172.4 grams | DI H$_2$O |

0.75% Gellan Solution

| | | |
|---|---|---|
| 0.75% | 7.5 grams | Gellan Gum (L/N 68014a) |
| 0.05% | 0.5 grams | Sodium Citrate (JT Baker) |
| 0.05% | 0.5 grams | Methyl Paraben (Spectrum) |
| 0.23% | 2.3 grams | Lecithin (Epikuron 100P1, Lucas Meyer Inc.) |
| 0.08% | 0.8 grams | Polyethylene Glycol 400 (Spectrum) |
| 98.84% | 988.4 grams | DI H$_2$O |

For both solutions, gellan gum and sodium Citrate were added to DI water and mixed with a high shear mixer. The solution was then heated to 70° C. Upon cooling, the remainder of the excipients was added. The solutions were sprayed at 40° C. to 50° C. 450 grams of the 1.5% gellan solution was sprayed onto red placebos to a 0.3% weight gain. An additional 610 grams of 0.75% solution was immediately sprayed on top of the placebos for an additional 0.2% weight gain. The two solutions provided a total gellan weight gain of 0.5%. No actives were sprayed this run. (J. T. Baker is a division of Mallinckrodt Baker, Inc., Philisburg, N.J. 08865 U.S.; Lucas Meyer Inc., P.O. Box 3218, Decatur, Ill., 62524–3218 U.S.; Spectrum Quality Products, Inc., New Brunswick, N.J. 08901 U.S.).

Example 2B

2.0% Gellan Gum Solution

| | | |
|---|---|---|
| 2.00% | 24.0 grams | Gellan (Kelco L/N) |
| 0.13% | 1.6 grams | Sodium Citrate (JT Baker) |
| 0.13% | 1.6 grams | Methyl Paraben (Spectrum) |
| 0.60% | 7.2 grams | Lecithin (Epikuron 100P1, Lucas Meyer Inc.) |
| 0.20% | 2.4 grams | Polyethylene Glycol 400 (Spectrum) |
| 96.94% | 1163.3 grams | DI H$_2$O |

0.75% Gellan Gum Solution

| | | |
|---|---|---|
| 0.75% | 7.5 grams | Gellan (Kelco L/N) |
| 0.05% | 0.5 grams | Sodium Citrate (JT Baker) |
| 0.05% | 0.5 grams | Methyl Paraben (Spectrum) |
| 0.23% | 2.3 grams | Lecithin (Epikuron 100P1, Lucas Meyer Inc.) |
| 0.08% | 0.8 grams | Polyethylene Glycol 400 (Spectrum) |
| 98.84% | 988.4 grams | DI H$_2$O |

For both solutions, gellan gum and Na Citrate were added to DI water and mixed with a high shear mixer. The solution was then heated to 70° C. Upon cooling, the remainder of the excipients was added. The solutions were sprayed at 40° C. to 50° C. 458 grams of the 2.0% gellan solution was sprayed onto red placebos to a 0.4% weight gain. An additional 305 grams of 0.75% solution was immediately sprayed on top of the placebos for an additional 0.1% weight gain. The two solutions provided a total gellan weight gain of 0.5%. No actives were sprayed this run.

Example 3B

1.5% Gellan Gum Solution

| | | |
|---|---|---|
| 1.50% | 18.0 grams | Gellan (Kelco) |
| 0.10% | 1.2 grams | Sodium Citrate (JT Baker) |
| 0.10% | 1.2 grams | Methyl Paraben (Spectrum) |
| .15% | 1.8 grams | Polyethylene Glycol 400 (Spectrum) |
| 98.15% | 1177.8 grams | DI H$_2$O |

0.75% Gellan Gum Solution

| | | |
|---|---|---|
| .75% | 7.5 grams | Gellan (Kelco) |
| .05% | 0.5 grams | Sodium Citrate (JT Baker) |
| .05% | 0.5 grams | Methyl Paraben (Spectrum) |
| .08% | 0.8 grams | Polyethylene Glycol 400 (Spectrum) |
| 99.07% | 990.7 grams | DI H$_2$O |

For both solutions, gellan and Na Citrate were added to DI water and mixed with a high shear mixer. The solution was then heated to 70° C. Upon cooling, the remainder of the excipients was added. The solutions were sprayed at 40° C. to 50° C. 412 grams of the 1.5% gellan solution was sprayed onto red placebos to a 0.27% weight gain. An additional 700 grams of 0.75% solution was immediately sprayed on top of the placebos for an additional 0.23% weight gain. The two solutions provided a total gellan weight gain of 0.5%. No actives were sprayed this run.

Example 4B

15% Gellan Gum Solution

| | | |
|---|---|---|
| 1.5% | 18.0 grams | Gellan (Kelco) |
| 0.1% | 1.2 grams | Sodium Citrate (JT Baker) |
| 0.1% | 1.2 grams | Methyl Paraben (Spectrum) |
| 0.15% | 1.8 grams | Polyethylene Glycol 400 (Spectrum) |
| 98.15% | 1177.8 grams | DI H$_2$O |

0.75% Gellan Gum Solution

| | | |
|---|---|---|
| 0.75% | 7.5 grams | Gellan (Kelco) |
| 0.05% | 0.5 grams | Sodium Citrate (JT Baker) |
| 0.05% | 0.5 grams | Methyl Paraben (Spectrum) |
| 0.08% | 0.8 grams | Polyethylene Glycol 400 (Spectrum) |
| 99.07% | 990.7 grams | DI H$_2$O |

For both solutions, gellan gum and Na Citrate were added to DI water and mixed with a high shear mixer. The solution was then heated to 70° C. Upon cooling, the remainder of the excipients was added. The solutions were sprayed at 40° C. to 50° C. 191 grams of the 1.5% gellan solution was sprayed onto actives to a 0.125% weight gain. An additional 229 grams of 0.75% solution was immediately sprayed on top of the actives for an additional 0.075% weight gain. The two solutions provided a total gellan gum weight gain of 0.2%.

Example 5B

| | | | |
|---|---|---|---|
| 1.5% Gellan | 1.5% | Gellan | 90 g |
| | 0.1% | Sodium Citrate | 6 g |
| | 0.1% | Methylparaben | 6 g |
| | 0.45% | Epikoron 100 P1 | 27 g |
| | 0.15% | PEG 400 | 9 g |
| | 97.7% | DI H$_2$O | 5862 g |
| | | | 6000 g total |
| 0.75% Gellan | 0.75% | Gellan | 7.5 g |
| | 0.05% | Na Citrate | 0.5 g |
| | 0.05% | MPB | 0.5 g |
| | 0.23% | Epikuron 100 P1 | 2.3 g |
| | 0.08% | PEG 400 | 0.8 g |
| | 98.84% | DI H$_2$O | 988.4 g |
| | | | 1000.0 g total |

1.5% and 0.75% Gellan — Placebo

| Time Min | Weight G | Flow Rate g/min | Total Volume L | Inlet ° Temp ° C. | Exhaust Temp ° C. | CFM | RPM | Atom. Air Psi |
|---|---|---|---|---|---|---|---|---|
| 0 | 0 | — | 0 | 71.0 | 56.0 | 268 | 23.1 | 23.4 |
| 6.0 | 134.3 | 22.4 | 0.138 | 72.3 | 49.9 | 277 | 22.9 | 22.3 |
| 12.0 | 258.8 | 20.8 | 0.262 | 71.9 | 50.5 | 274 | 22.9 | 21.9 |
| 16.0 | 333.0 | 18.5** | 0.363 | 72.0 | 50.6 | 272 | 22.9 | 21.8 |
| 25.5 | 222.4 | 23.4 | 0.563 | 71.9 | 50.3 | 271 | 20.0 | 21.6 |
| 31.0 | 352.5 | 23.7 | 0.686 | 70.7 | 50.4 | 274 | 20.0 | 21.6 |
| 37.5 | 509.2 | 24.01 | 0.837 | 71.0 | 50.5 | 269 | 20.0 | 21.5 |
| 47.5 | *735.0 | — | 1.058 | 70.1 | 50.6 | 271 | 20.0 | 21.4 |

*For a 0.5 Gellan wt. Gain total.
**Scale reset to zero after 333 g.

Acceptable tablets had very high gloss. No problems converting from 1.5–0.75% Gellan. Run saved 20 minutes off of a regular 0.75% Gellan Run.

Example 6B 2.0% Gellan (0.4% wt. Gain) 0.75% Gellan (Final 0.1% wt. Gain) onto placebos.

| Time Min | Weight G | Flow Rate g/min | Total Volume L | Inlet ° Temp ° C. | Exhaust Temp ° C. | CFM | RPM | Atom. Air Psi |
|---|---|---|---|---|---|---|---|---|
| 0 | 0 | — | 0 | 71.0 | 55.6 | 282 | 23.0 | 23.6 |
| 3.0 | 55.6 | 18.5 | 0.060 | 71.1 | 52.3 | 270 | 23.0 | 22.2 |
| 17.0 | 233.8 | 12.8 | 0.234 | 71.0 | 55.9 | 271 | 23.0 | 22.0 |
| 25.0 | 373.5 | **17.5 | 0.379 | 71.1 | 52.9 | 277 | 20.0 | 21.7 |
| 29.0 | 24.5 | — | 0.417 | 70.1 | 54.6 | 274 | 20.0 | 21.6 |
| 33.0 | 107.5 | 20.8 | 0.498 | 68.8 | 50.7 | 272 | 20.0 | 21.6 |
| 38.5 | 252.8 | 26.4 | 0.640 | 71.2 | 50.2 | 279 | 20.0 | 21.6 |
| 39.5 | *305.0 | — | 0.714 | 70.1 | 50.8 | 274 | 20.0 | 21.5 |

*For a 0.5% total wt. Gain.
**Pulled hose from 2.0% solution and placed into 0.75%, tared scale.

Run yielded tablets with acceptable gloss. 2.0% Gellan sprayed with no problem. 458 g of 2.0% was sprayed before switching to the 0.75% solution. 305 g of 0.75% was sprayed. This gave a total wt. Gain of 0.5% (0.4% from 2% solution and 0.1% wt gain from 0.75% solution).

Example 7B

| | | Flow | Total | Inlet ° | Exhaust | | | Atom. |
|---|---|---|---|---|---|---|---|---|
| Time | Weight | Rate | Volume | Temp | Temp | | | Air |
| Min | G | g/min | L | ° C. | ° C. | CFM | RPM | Psi |

1.5% Gellan and 0.75% Gellan (both without Epikuron) onto placebos

| Time Min | Weight G | Flow Rate g/min | Total Volume L | Inlet ° Temp ° C. | Exhaust Temp ° C. | CFM | RPM | Atom. Air Psi |
|---|---|---|---|---|---|---|---|---|
| 0 | 0 | — | 0 | 71.1 | 56.1 | 282 | 23.0 | 24.2 |
| 3.5 | 71.3 | 20.4 | 0.077 | 71.0 | 51.1 | 281 | 23.1 | 23.9 |
| 8.5 | 170.3 | 19.8 | 0.178 | 71.1 | 51.4 | 282 | 23.0 | 23.8 |
| 15.0 | 322.2 | 23.4 | 0.336 | 71.9 | 50.9 | 271 | 23.0 | 23.7 |
| 22.0 | 0** | — | 0.451 | 72.0 | 57.2 | 284 | 20.0 | 23.7 |
| 27.0 | 133.3 | 26.7 | 0.573 | 72.0 | 52.3 | 285 | 20.0 | 23.6 |
| 38.5 | 445.4 | 22.1 | 0.871 | 71.0 | 50.8 | 278 | 20.0 | 23.3 |
| — | *700.0 | 0 | 1.190 | 71.0 | 50.2 | 281 | 20.0 | 23.2 |

*For a 0.5% Gellan wt. Gain. Tablets have an excellent gloss.
**Scale Reset

Example 8B 1.5% Gellan and 0.75% Gellan onto actives

| Time Min | Weight G | Flow Rate g/min | Total Volume L | Inlet ° Temp ° C. | Exhaust Temp ° C. | CFM | RPM | Atom. Air Psi |
|---|---|---|---|---|---|---|---|---|
| 0 | 0 | — | 0 | 70.8 | 55.9 | 274 | 23.0 | 23.7 |
| 3.0 | 66.0 | 22.0 | 0.096 | 71.0 | 51.7 | 279 | 23.0 | 23.5 |
| 6.5 | 125.0 | 16.9 | 0.135 | 71.0 | 50.5 | 277 | 23.0 | 23.4 |
| 6.5 | 0 | *— | 0.135 | 71.0 | 50.5 | 277 | 23.0 | 23.4 |
| 11.0 | 162.5 | — | 0.250 | 71.0 | 50.2 | 274 | 22.9 | 23.4 |
| — | **229.0 | — | 0.327 | 71.0 | 50.4 | 281 | 20.0 | 23.3 |

*Scale reset.
**For a 0.2% Gellan wt. Gain. Tablets and caplets look acceptable at 0.2% with very high gloss.

Example 9B

| 850 grams | 1.5% Gellan solution* |
| 10.625 grams | Titanium dioxide dispersion** |
| 2.55 grams | Epikuron 200SH |
| 5.1 grams | Propylene Glycol |

Gellan solution heated to 50 degrees C. Titanium dioxide dispersion, Epikuron 200 SH and Propylene Glycol are added. Once dispersed, 420 grams total (3/8" standard concave) with 15 Celebrex tablets were coated with 552 grams (50 degrees C.) to a 3.0% weight gain.

Example 10B

| 97.9% | 200 grams | 1.5% Gellan solution* |
| 0.6% | 1.2 grams | Propylene Glycol |
| 0.3% | 0.6 grams | Epikuron 200 SH |
| 1.2% | 2.5 grams | Titanium dioxide dispersion** |

Gellan solution heated to 50 degrees C. Titanium dioxide dispersion, Epikuron 200 SH and Propylene Glycol are added. Once dispersed, 420 grams total (3/8" standard concave) with 15 Celebrex tablets were coated with 80 grams (50 degrees C.) to a 0.5% weight gain. Immediately, an additional 0.5% weight gain (116 grams) of 1.5% gellan solution was applied as a clear overcoat.

Results

Coated tablets were shiny, smooth, white with good mouthfeel.
*1.5% Gellan solution:
12.75 grams Gellan
0.85 grams Sodium Citrate
0.85 grams Methyl Paraben
836 grams Deionized water
**Titanium dioxide dispersion:

| 60% | 150 grams | Titanium Dioxide |
| 33.6% | 84 grams | Deionized water |
| 6.4% | 16 grams | 10% EDTA solution |

Thus, it is seen from the aforegoing examples that this gellan gum coating can be made and used for actives including ibuprofen, naproxen sodium, acetaminophen, sildenafil citrate, celecoxib, oxaprozin, alendronate sodium, mixtures thereof and the like, as well as an analgesic in some combination with one or more of antihistamine, antitussive, decongestant, expectorant, mixtures thereof and the like.

Gellan with Hydrocolloid Blends

Carrageenan, Guar and Locust Bean Gums used for testing was made by TIC Gums, Inc. 4609 Richlynn Drive, P.O. Box 369, Bellcamp, Md. 21017.
15" Accela-Cota trails spraying hydrocolloid onto actives:
Charge: Ibuprofen tablets were added to uncoated 3/8" concave placebos where final charge is 1.9 kg.

Example 11B

| | | |
|---|---|---|
| 98.5% | 1477.5 grams | Deionized Water |
| 1.0% | 15 grams | Gellan Gum |
| 0.50% | 7.5 grams | Guar Gum (TIC Gums, Inc.) |

Add Guar and Gellan gum to DI water and heat to 70 degrees C., once dissolved, sprayed 745 grams (50 degrees C.) onto tablets to a 0.5% weight gain* on placebos.

Example 12B

| | | |
|---|---|---|
| 98.5% | 1477.5 grams | Deionized Water |
| 1.25% | 18.75 grams | Gellan Gum |
| 0.25% | 3.75 grams | Carrageenan (TIC Gums, Inc.) |

Add Carrageenan and Gellan gum to DI water and heat to 70 degrees C, once dissolved, sprayed 745 grams (50 degrees C) onto tablets to a 0.5% weight gain* on placebos.

Example 13B

| | | |
|---|---|---|
| 98.5% | 1477.5 grams | Deionized Water |
| 1.25% | 18.75 grams | Gellan Gum, Lot |
| 0.25% | 3.75 grams | Locust Bean Gum (TIC Gums, Inc.) |

Pass Locust Bean gum through USP 200 screen to remove/break up impurities/insoluble particles. Add Locust Bean gum and Gellan Gum to DI water, initially heat to 70 degrees C., once dissolved, sprays 745 grams (50 degrees C.) onto tablets to a 0.50% weight gain*.
*Actives were only coated to a 0.20% weight gain.

Thus, it is apparent that there has been provided, in accordance with the instant invention, an invention that fully satisfies the objects and advantages set forth herein above. While the invention has been described with respect to various specific examples and embodiments thereof, it is understood that the invention is not limited thereto and many alternatives, modifications and variations will be apparent to those skilled in the art in light of the foregoing description. Accordingly, it is intended to embrace all such alternatives, modifications and variations as fall within the spirit and broad scope of the invention.

What is claimed is:

1. An intact coated active tablet having a weight of about 25 mg to about 2 g and comprising an active ingredient selected from the group consisting of aspirin, ibuprofen, naproxen sodium, acetaminophen, celecoxib, oxaprozin, sildenafil citrate, alendronate sodium and an analgesic in combination with one or more of antitussive, antihistamine, decongestant, and expectorant, prepared by spraying the tablet with an aqueous composition comprising from about 0.5 wt % to about 3 wt % gellan gum wherein the gellan gum is the principal component of the aqueous composition.

2. The tablet of claim 1 wherein the aqueous composition further comprises at least one selected from a color, a plasticizer, and a surfactant.

3. The tablet of claim 1 wherein the aqueous composition forms a primary coating.

4. The tablet of claim 1 further comprising coating the tablet with a composition comprising a polymer other than gellan gum.

5. The tablet of claim 4 wherein the composition comprising a polymer other than gellan gum forms a primary coating.

6. The tablet of claim 1 wherein the coating comprising gellan gum is the only coating.

7. The tablet of claim 1 wherein the level of gloss is about 200 to about 400 when analyzed using a surface system analyzer.

8. The tablet of claim 7 wherein the level of gloss is about 250 to about 350.

9. The tablet of claim 1 wherein the active ingredient is aspirin.

10. The tablet of claim 1 wherein the coating further comprises at least one selected from the group consisting of sugar, calcium, sorbitol, mannitol, maltose, maltitol, xylitol, and mixtures thereof.

11. An intact coated active tablet having a weight of about 25 mg to about 2 g and comprising an active ingredient tablet and a dried coating, the active ingredient selected from the group consisting of aspirin, ibuprofen, naproxen sodium, acetaminophen, celecoxib, oxaprozin, sildenafil citrate, alendronate sodium and an analgesic in combination with one or more of antitussive, antihistamine, decongestant, and expectorant; the dried coating comprising about 0.025% to about 10% by weight of the total tablet; the coated tablet prepared by spraying a tablet with an aqueous composition comprising from about 0.5 wt % to about 3 wt % gellan gum, and drying.

12. The tablet of claim 11 wherein the dried coating comprises about 0.05% to about 5% by weight of the total tablet.

13. The tablet of claim 12 wherein the dried coating comprises about 0.1% to about 1% by weight of the total tablet.

14. The tablet of claim 11 wherein the aqueous composition further comprises at least one selected from a color, a plasticizer, and a surfactant.

15. The tablet of claim 11 wherein the level of gloss is about 200 to about 400 when analyzed using a surface system analyzer.

16. The tablet of claim 15 wherein the level of gloss is about 250 to about 350.

17. The tablet of claim 11 wherein the active ingredient is aspirin.

18. The tablet of claim of 11 claim wherein the coating further comprises at least one selected from the group consisting of sugar, calcium, sorbitol, mannitol, maltose, maltitol, xylitol, and mixtures thereof.

\* \* \* \* \*